United States Patent [19]

Nesvadba et al.

[11] 4,055,642
[45] Oct. 25, 1977

[54] IMIDAZOLYL-2-QUINAZOLINE DERIVATIVES

[75] Inventors: Hans Nesvadba; Hellmuth Reinshagen, both of Vienna, Austria

[73] Assignee: Sandoz Ltd., Basel, Switzerland

[21] Appl. No.: 683,291

[22] Filed: May 5, 1976

[30] Foreign Application Priority Data

May 12, 1975 Switzerland ............... 6041/75

[51] Int. Cl.² ............ A61K 31/505; C07D 239/88; C07D 239/93; C07D 239/94
[52] U.S. Cl. .................. 424/246; 544/62; 544/119; 260/256.4 Q; 424/248.56; 424/251; 424/248.57
[58] Field of Search ........ 260/251 Q, 251 QA, 243 B, 260/247.5 DP, 256.4 Q; 424/251, 246, 248

[56] References Cited
U.S. PATENT DOCUMENTS

| | | | |
|---|---|---|---|
| 3,324,122 | 6/1967 | Burch | 260/251 Q |
| 3,705,898 | 12/1972 | Alaimo | 260/251 Q |
| 3,920,655 | 11/1975 | Rufer et al. | 424/251 |

*Primary Examiner*—Paul M. Coughlan, Jr.
*Attorney, Agent, or Firm*—Gerald D. Sharkin; Robert S. Honor; Thomas O. McGovern

[57] ABSTRACT

Basically substituted imidazolyl-2-quinazolines of the formula

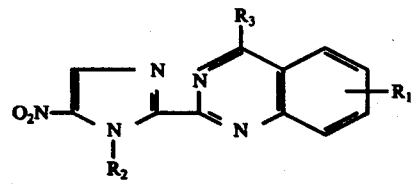

where
R₁ is hydrogen, lower alkyl or halogen;
R₂ is lower alkyl, lower alkenyl or lower hydroxalkyl; and
R₃ is a basic organic substituent, are useful as anti-parasitic agents and as mycoplasma growth inhibiting agents.

31 Claims, No Drawings

IMIDAZOLYL-2-QUINAZOLINE DERIVATIVES

The invention relates to imidazolylquinazoline derivatives.

More particularly, this invention provides compounds of formula I,

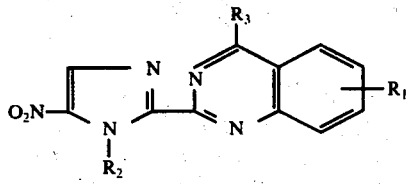

I in which
$R_1$ is hydrogen, lower alkyl or halogen,
$R_2$ is lower alkyl, lower alkenyl or lower hydroxyalkyl, and
$R_3$ is
 a. a group of formula II,

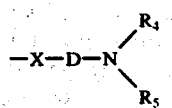

II in which
 X is oxygen or sulphur,
 D is straight or branched chain alkylene,
and either
 $R_4$ is hydrogen or lower alkyl, and
 $R_5$ is lower alkyl or lower hydroxyalkyl,
or
 $R_4$ and $R_5$, together with the nitrogen atom to which they are attached, signify a six-membered, saturated, heterocyclic radical, which may contain a second ring nitrogen atom, unsubstituted or substituted by lower alkyl or lower hydroxyalkyl,
 b. a group of formula III,

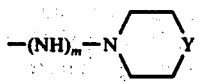

III in which
 $m$ is 0 or 1, and
 Y is oxygen or sulphur, or imino, unsubstituted or substituted by lower alkyl or lower hydroxyalkyl,
 c. a group of formula IV,

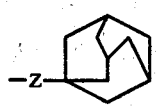

IV in which Z is —NH— or

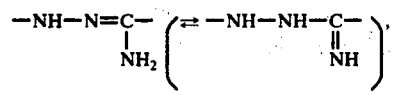

d. a group of formula V,

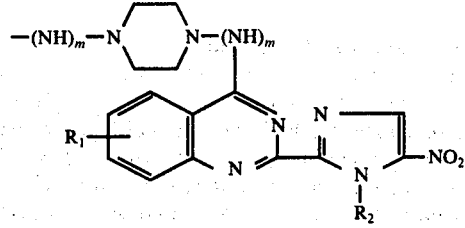

in which
 $m$, $R_1$ and $R_2$ are as defined above,
 the $m$'s, the $R_1$'s and the $R_2$'s then being the same,
 e. a group of formula VI,

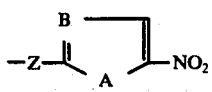

VI in which
 Z is as defined above, and
either
 A is oxygen or sulphur and
 B is =CH—,
or
 A is sulphur or —N($R_6$)—, in which $R_6$ is lower alkyl or lower hydroxyalkyl,
and
 B is nitrogen,
or
 f. a group of formula VII,

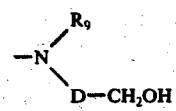

VII in which
 D is as defined above, and
 $R_9$ is hydrogen, lower alkyl or lower hydroxyalkyl.

In a first class of compounds $R_3$ is a group of formula I stated above. In this case, D, $R_4$ and $R_5$ have the following preferred significances:
 D: straight or branched alkylene of 1 to 6, preferably 2 or 3, carbon atoms, in particular dimethylene or 1,2-propylene;
 i. either $R_4$: hydrogen or lower alkyl of 1 to 4, particularly 1 to 2 carbon atoms, in particular hydrogen or ethyl
 and
 $R_5$: lower alkyl of 1 to 4, particularly 1 to 2, carbon atoms or lower hydroxyalkyl of 1 to 4, in particular 2, carbon atoms, preferably ethyl or hydroxyethyl;
 or
 ii. $R_4$ and $R_5$: together with the nitrogen atom to which they are attached signify piperidino or piperazino, in particular piperazino unsubstituted or substituted on the second nitrogen atom by lower alkyl of 1 to 4, in particular 1 or 2, carbon atoms, or lower hydroxyalkyl of 1 to 4, in particular 2, carbon atoms, more particularly by hydroxyethyl;
 X: as defined above, preferably sulphur.

The most preferred compounds in this class have combinations of the above preferred significances of D, $R_4$, $R_5$ and X.

In a second class of compounds, $R_3$ is a group of formula III. In this case, m is preferably O and Y is as defined above. When Y is imino, it is preferably unsubstituted or substituted by lower alkyl of 1 to 4, in particular 1 or 2, carbon atoms, or lower hydroxyalkyl of 1 to 4, in particular 2, carbon atoms; more preferably it is unsubstituted or substituted by methyl or hydroxyethyl.

In a third class of compounds, $R_3$ is a group of formula IV.

In a fourth class of compounds, $R_3$ is a group of formula V. In this case, each m is preferably O.

In a fifth class of compounds, $R_3$ is a group of formula VI. In this event, Z is preferably

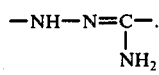

In one preferred class of such compounds, A is oxygen and B is —CH—. In another, B is nitrogen and A is —N($R_6$)—. $R_6$ is preferably lower alkyl of 1 to 4, in particular 1 to 2, carbon atoms or lower hydroxyalkyl of 1 to 4, preferably 2, carbon atoms, more preferably lower alkyl, in particular methyl or ethyl, more particularly methyl.

In a sixth class of compounds, $R_3$ is a group of formula VII. In this case, D suitably signifies straight or branched alkylene of 1 to 6, in particular 1 to 3 carbon atoms, more particularly methylene. $R_9$ preferably signifies hydrogen or lower alkyl of 1 to 4, in particular 1 to 2, carbon atoms, more preferably hydrogen or methyl.

In all classes of compounds described above, $R_1$ preferably signifies hydrogen, lower alkyl of 1 to 4, in particular 1 to 2 carbon atoms, or halogen, in particular fluorine, chlorine, bromine or iodine, more particularly chlorine; more preferably $R_1$ is hydrogen, methyl or chlorine. When $R_1$ is other than hydrogen, it is preferably in the 6 or 7-position of the quinazoline nucleus.

In all classes of compounds described above, $R_2$ preferably signifies lower alkyl of 1 to 6, in particular 1 to 2 carbon atoms, lower alkenyl of 2 to 6 carbon atoms, in particular vinyl or allyl, or lower hydroxyalkyl of 1 to 6, in particular 2 carbon atoms; more preferably, $R_2$ is lower alkyl, in particular methyl.

The invention also provides a process for the production of compounds of formula I characterised by reacting a compound of formula VIII,

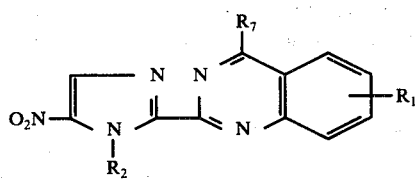

VIII in which
$R_1$ and $R_2$ are as defined above,
and
$R_7$ is halogen,
with a compound of formula IX,

 IX in which $R_3{}^I$ is a group of formula II, III, IV, VI or VII, stated above, or when a compound of formula I, in which $R_3$ is a group of formula V, stated above, is desired, a group of formula X,

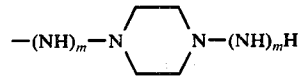

X in which
m is as defined above, in the absence of water.

The reaction is suitably effected in an anhydrous, inert organic solvent, for example an aromatic or aliphatic, optionally chlorinated, hydrocarbon solvent, for example benzene or chloroform, or a di(lower)alkylamide, such as dimethyl formamide, conveniently by adding the compound IX to a solution or suspension of the compound VIII in said solvent. The reaction is conveniently effected at an elevated temperature, particularly at the reflux temperature of the reaction mixture. The reaction can alternatively be effected, in the absence of solvent, by melting the reaction components together. As will be appreciated, where $R_3'$ is a group of formula X, the reaction is desirably effected using two moles of the compound VIII per mole of the compound IX. $R_7$ is preferably chlorine or bromine.

It will be appreciated that the starting materials of formula IX required for the production of compounds of formula I, in which $R_3$ is a group of formula VII in which $R_9$ is other than hydrogen are the same as those required for the production of compounds of formula I in which $R_3$ is a radical of formula II, in which X is oxygen and $R_4$ is hydrogen. In order to produce the compounds in which $R_3$ is a group of formula VII, the process is suitably effected in an alkaline medium, conveniently provided by employing an excess of the compound of formula IX, whereas to favour production of the compounds in which $R_3$ is a radical of formula II, the process is preferably effected in a neutral medium, in particular employing a 1:1 molar ratio of the compounds of formulae VIII and IX.

The resulting compounds of formula I may be isolated and purified using conventional techniques.

The compounds of formula VIII are new and may be produced by halogenating a compound of formula XI,

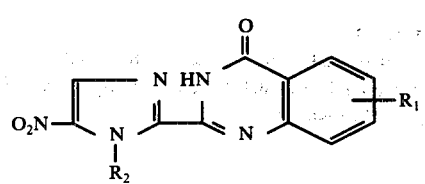

XI in which $R_1$ and $R_2$ are as defined above.

The reaction can be carried out employing conventional halogenating agents and conditions for such reactions, for example employing phosphorous pentachloride and an elevated temperature, particularly reflux temperature, and excluding water.

The compounds of formula XI are also new and may be prepared by condensing a compound of formula XII,

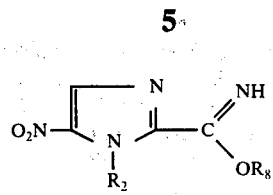

in which
R₂ is as defined above, and
R₈ is lower alkyl,
with a compound of formula XIII,

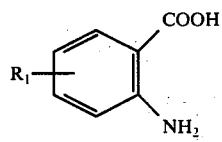

in which R₁ is as defined above.

The condensation is suitably effected in an inert organic solvent, for example a lower alcohol, such as methanol or ethanol, or a di(lower)alkylamide, such as dimethylformamide, and preferably at room temperature or an elevated temperature. Alternatively, the condensation may be effected in the absence of solvent by melting the reaction components together.

The compounds of formula I are useful because they possess chemotherapeutic activity. In particular, they possess anti-parasitic activity, more particularly against amoeba and trichomonads, and are therefore useful as anti-parasitic, in particular amoebicidal and anti-trichomonad agents. The amoebicidal and anti-trichomonad activity is indicated in vitro by determination of the minimum lethal concentration (MLC) in the series dilution test after 48 hours incubation at 37° C. The amoebicidal activity is determined in a TTY-SB medium against monoxenically cultivated E. histolytica amoeba [Diamond, L.S., J. Parasit. 54, 715 (1968)] at concentrations of about 0.8 to 100 μg/ml. The anti-trichomonad activity is determined by addition of the test substance to a T. vaginalis culture in a CACH medium [Müller et al., Angew Parasit. 11, 170 (1970)] at concentrations of about 0.005 to 0.4 μg/ml. The anti-trichomonad activity is confirmed in vivo in the mouse and rat, and the amoebicidal activity is confirmed *in vivo* in the rat and hamster, at a dosage of 1.5 to 150 mg/kg of animal body weight administered thrice.

For the above-mentioned uses, the dosage aministered will, of course, vary depending on the compound employed, mode of administration and treatment desired. However, for the treatment of amoebiasis and trichomoniasis, in general satisfactory results are obtained when administered at a daily dosage of about 5 to 150 mg/kg or 5 to 300 mg/kg of animal body weight, respectively, conveniently given in divided dosages two to four times daily. For the larger mammals, the corresponding total daily dosages are in the range, respectively of about 400 to 3000 mg and 250 to 700 mg, and dosage forms suitable for oral administration comprise from about 100 to 1,500 mg and 62.5 to 350 mg, respectively.

For these uses, preferred compounds include 2-(1-methyl-5-nitro-2-imidazolyl)-4-{2-[4-(2-hydroxyethyl)-1-piperazinyl]ethylthio}quinazoline and 2-(1-methyl-5-nitro-2-imidazolyl)-4-[2-(diethylamino)ethyl-thio]-quinazoline.

The compounds of formula I also possess inhibiting activity against mycoplasma and are therefore useful as mycoplasma growth inhibiting agents. This activity is indicated in vitro by determination of the minimum inhibiting concentration (MIC) using the series dilution test after 48 hours incubation at 37° C at concentrations of from about 0.8 to 6.2 μg/ml using various strains, including *M. hominis, M. gallisepticum, M. hyorhinis* and *M. arthritidis*. The activity may be confirmed in vivo in the rat polyarthritis model using M. arthritidis.

For the above-mentioned use, the dosage administered will, of course, vary depending on the compound employed, mode of administration and treatment desired. However, in general satisfactory results are obtained when administered at a daily dosage of about 50 to 200 mg/kg of animal body weight, conveniently administered in divided dosages two to four times daily. For the larger mammals, the total daily dosage is in the range of 3.5 to 10 g and dosage forms suitable for oral administration comprise about 1 to 5 g.

For this use, the preferred compounds include 2-(1-methyl-5-nitro-2-imidazolyl)-4-{2-[4-(2-hydroxyethyl)-1-piperazinyl]ethylthio}quinazoline and 2-(1-methyl-5-nitro-2-imidazolyl)-4-{2-[(2-hydroxyethyl)-amino]ethoxy}-6-methyl quinazoline.

For the above-mentioned uses, the compounds may be admixed with conventional chemotherapeutically acceptable diluents or carriers and administered in such forms as tablets, capsules or injectable solutions. For use in inhibiting mycoplasma growth in animals the compounds may suitably be administered as injectable solutions or as a component of drinking water.

The compounds may be used in free base form or in the form of chemotherapeutically acceptable acid addition salts, which salt forms have the same order of activity as the free base forms. Suitable acids for salt formation include hydrochloric acid.

The following Examples illustrate the invention.

EXAMPLE 1

2-(1-Methyl-5-nitro-2-imidazolyl)-4-{2-[(2-hydroxyethyl)amino]ethoxy}quinazoline a. 2-(1-Methyl-5-nitro-2-imidazolyl)-4-quinazolinone A solution of 20.4 g of 1-methyl-5-nitro-2-imidazolyl-carbiminoethyl ether and 14.1 g of 2-aminobenzoic acid in 245 ml of methanol is allowed to stand for 6 days at room temperature. The resulting crystals are filtered off, washed with methanol and dried, to obtain the heading compound, m.p. 256°–260° C.

b. 2-(1-Methyl-5-nitro-2-imidazolyl)-4-chloroquinazolin

A suspension of 25 g of 2-(1-methyl-5-nitro-2-imidazolyl)-4-quinazolinone and 26.2 g of phosphorus pentachloride in 150 ml of phosphorus oxychloride is boiled for 3 hours and then evaporated in vacuo (12 Torr). The residue is taken up in methylene chloride and stirred with water for one hour at room temperature. The mixture is made alkaline with sodium bicarbonate and extracted by dropwise addition of methylene chloride. The mixture is dried with magnesium sulphate and treated with animal charcoal, filtered and evaporated in vacuo (12 Torr) at 30° C. The residue is mixed with ether, filtered and washed pure with ether to obtain the heading compound, m.p. 178°–181° C.

c. 2-(1-Methyl-5-nitro-2-imidazolyl)-4-{2-[(2-hydroxyethyl)amino]ethoxy}quinazoline A suspension of 4 g of 2-(1-methyl-5-nitro-2-imidazolyl)-4-chloroquinazolin and 1.6 g of diethanolamine in 25 ml of dimethyl formamide is heated at 100° C for 1½ hours. After cooling, the resulting crystals are filtered off, washed with tetrahydrofuran and water, and dried to obtain the heading compound, m.p. 236°-239° C.

In manner analogous to Example 1, employing appropriate starting materials in approximately equivalent amounts, the compounds of formula I in the following Table (Examples 2 to 41) may be obtained.

| Ex. No. | $R_1$ | $R_2$ | $R_3$ | M.P. (°C) |
|---|---|---|---|---|
| 2 | H | $CH_3$ | —SCH₂CH₂N⟨piperazine⟩N—CH₂CH₂OH  | 240-245° |
| 3 | H | $CH_3$ | —NH—NH—C(=NH)—adamantyl 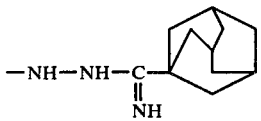 | 290-293° |
| 4 | H | $CH_3$ | —N⟨thiomorpholine⟩S 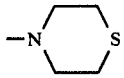 | 209-221° |
| 5 | H | $CH_3$ | —SCH₂CH₂N(C₂H₅)₂ | 106-109° |
| 6 | H | $CH_3$ | —SCH₂CH₂N⟨piperazine⟩N—CH₃ 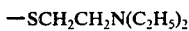 | 150-153° |
| 7 | H | $CH_3$ | —NH—adamantyl 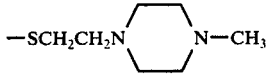 | 216-218° |
| 8 | H | $CH_3$ | —N⟨piperazine⟩N—CH₃ 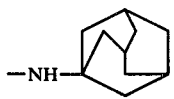 | 274-276° (decomp) |
| 9 | H | $CH_3$ | —NH—N=C(NH₂)—furan—NO₂ 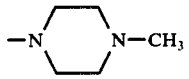 | 280-285° |
| 10 | H | $CH_3$ | OCH(CH₃)CH₂NHCH₂CH(CH₃)OH | 230-232° |
| 11 | H | $CH_3$ | —NHCH₂CH₂OH | 253-257° |
| 12 | 7-Cl | $CH_3$ | —OCH₂CH₂NHCH₂CH₂OH | 98-103° |
| 13 | 6-$CH_3$ | $CH_3$ | —OCH₂CH₂NHCH₂CH₂OH | 224-228° |
| 14 | 6-$CH_3$ | $CH_3$ | —SCH₂CH₂N⟨piperazine⟩NCH₂CH₂OH 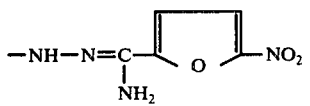 | 145-148° |
| 15 | H | $CH_3$ | —N⟨piperazine⟩N—CH₂CH₂OH  | 261-263° |
| 16 | H | $CH_3$ | —N⟨morpholine⟩O 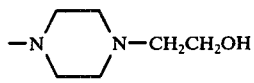 | 227-230° |
| 17 | H | $CH_3$ | —N(CH₃)CH₂CH₂OH | 175-178° |
| 18 | H | $CH_3$ | —NH—N=C(NH₂)—imidazole—NO₂ 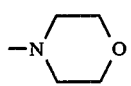 | 312-316° |

-continued

| | | | | |
|---|---|---|---|---|
| 19 | H | CH₃ | 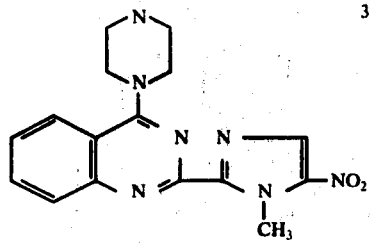 | 337–342° |
| 20 | 6-Cl | CH₃ | 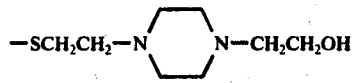 —SCH₂CH₂N⟨piperazine⟩N—CH₂CH₂OH | 132–135° |
| 21 | 6-Cl | CH₃ | —OCH₂CH₂NHCH₂CH₂OH | 158–162° |
| 22 | 7-Cl | CH₃ | 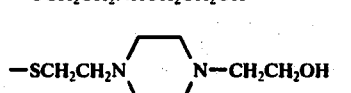 —SCH₂CH₂N⟨piperazine⟩N—CH₂CH₂OH | 140–146° |
| 23 | H | CH₃ | —SCH₂CH₂N(C₂H₅)CH₂CH₂OH | 235–240° |
| 24 | H | —CH₂CH₃ | —SCH(CH₃)CH₂NHCH₂CH(CH₃)OH | |
| 25 | 6-Cl | —CH₂—CH=CH₂ | —OCH₂CH₂N(C₂H₅)₂ | |
| 26 | 7-CH₃ | —CH₂CH₂OH | 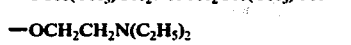 —OCH₂CH₂N⟨piperazine⟩NCH₂CH₂OH | |
| 27 | H | CH₃ | 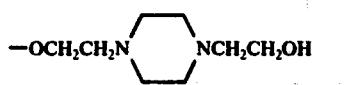 —SCH₂CH₂N⟨piperazine⟩NH | |
| 28 | 6-Br | —CH₂CH₃ |  —SCH₂CH₂N⟨piperidine⟩ | |
| 29 | 6-CH₃ | —CH₂—CH=CH₂ |  —NH—NH—C(=NH)—adamantyl | |
| 30 | 7-Cl | —CH₂CH₂OH |  —NH—adamantyl | |
| 31 | 6-CH₃ | —CH₂CH₃ |  —NH—N⟨piperazine⟩NCH₃ | |
| 32 | 7-Cl | —CH₂—CH=CH₂ | 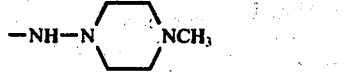 —N⟨thiomorpholine⟩ | |
| 33 | H | —CH₂CH₂OH |  —N⟨morpholine⟩ | |
| 34 | 6-Cl | —CH₂—CH₃ |  —NH—N⟨piperazine⟩N—NH | |

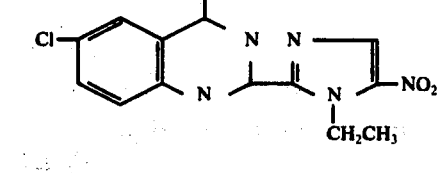

-continued

| | | |
|---|---|---|
| 35 | 6-CH$_3$ —CH$_2$CH$_2$OH | 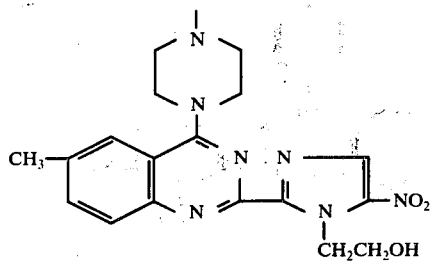 |
| 36 | 7-Cl —CH$_2$CH$_3$ | 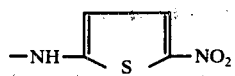 |
| 37 | 6-CH$_3$ —CH$_2$CH=CH$_2$ | 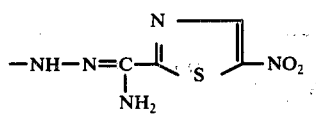 |
| 38 | H —CH$_2$CH$_2$OH | 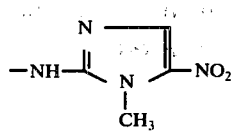 |
| 39 | 6-Cl —CH$_2$CH$_3$ | —N(CH$_3$)CH$_2$CH$_2$OH |
| 40 | 7-CH$_3$ —CH$_2$—CH=CH$_2$ | —N(CH$_2$CH$_2$OH)$_2$ |
| 41 | H —CH$_2$CH$_2$OH | —N(CH$_2$CH$_2$OH)$_2$ |

EXAMPLE 42

2-(1-Methyl-5-nitro-2-imidazolyl)-4-[N-di(2-hydroxyethyl)amino]quinazoline

A suspension of 6 g of 2-(1-methyl-5-nitroimidazolyl)4-chloroquinazoline and 12 g of diethanolamine in 40 ml of dimethylformamide is heated at 100° C for 1 hour in the absence of moisture. The mixture is cooled and mixed with distilled water and the resulting crystals are filtered off and dissolved in chloroform. The solution is dried with magnesium sulphate treated with animal charcoal and filtered and the filtrate is evaporated. The oily residue is mixed with ether and the resulting crystals filtered off, washed with ether and dried at room temperature in a water-jet vacuum, to obtain the heading compound, m.p. 175°–177° C.

The compounds of the foregoing Examples 1 to 23 and 42, in particular Examples 2 and 5 are useful as amoebicidal, trichomonadicidal and mycoplasma growth inhibiting agents, at dosages of for example 50 to 150, 5 to 300 and 50 to 200 mg/kg of animal body weight, respectively.

What is claimed is:
1. Compounds of formula I,

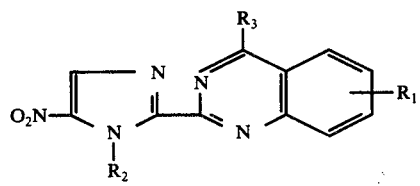

I in which
R$_1$ is hydrogen, lower alkyl of 1 to 4 carbon atoms or halogen,

R$_2$ is lower alkyl of 1 to 6 carbon atoms, lower alkenyl of 2 to 6 carbon atoms or lower hydroxyalkyl of 1 to 6 carbon atoms, and
R$_3$ is
a. a group of formula II,

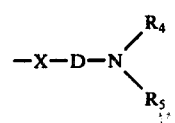

II in which
X is oxygen or sulphur,
D is straight or branched chain alkylene of 1 to 6 carbon atoms
and either
R$_4$ is hydrogen or lower alkyl of 1 to 4 carbon atoms
and
R$_5$ is lower alkyl of 1 to 4 carbon atoms or lower hydroxyalkyl of 1 to 4 carbon atoms
or
R$_4$ and R$_5$, together with the nitrogen atom to which they are attached, is piperidino or piperazino, unsubstituted or substituted by lower alkyl of 1 to 4 carbon atoms or lower hydroxyalkyl of 1 to 4 carbon atoms.
b. a group of formula III,

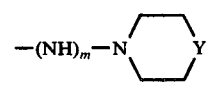

III in which
m is 0 or 1, and

Y is oxygen or sulphur, or imino, unsubstituted or substituted by lower alkyl of 1 to 4 carbon atoms or lower hydroxyalkyl of 1 to 4 carbon atoms c. a group of formula IV,

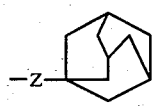

IV in which
Z is —NH—or

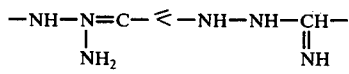

d. a group of formula V,

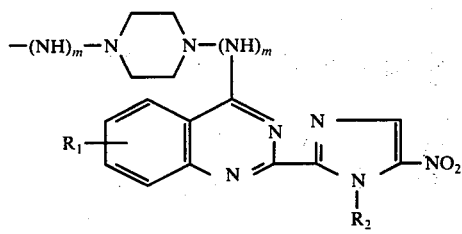

in which
  m, $R_1$ and $R_2$ are as defined above, the m's, the $R_1$'s and the $R_2$'s then being the same, e. a group of formula VI,

VI

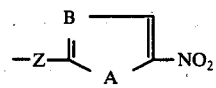

in which
Z is a defined above, and
either
  A is oxygen or sulphur and B is —CH—,
or
  A is sulphur or —N($R_6$)—, in which $R_6$ is lower alkyl of 1 to 4 carbon atoms or lower hydroxyalkyl of 1 to 4 carbon atoms,
and
  B is nitrogen,
or f. a group of formula VII,

VII

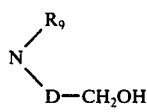

in which
  D is a defined above, and
  $R_9$ is hydrogen, lower alkyl of 1 to 4 carbon atoms or lower hydroxyalkyl of 1 to 4 carbon atoms
and chemotherapeutically acceptable acid addition salts thereof.

2. Compounds of claim 1, in which $R_3$ is a radical II, defined in claim 1.

3. Compounds of claim 2, in which $R_4$ is hydrogen or lower alkyl and $R_5$ is lower alkyl or lower hydroxyalkyl.

4. Compounds of claim 2, in which $R_4$ and $R_5$ together with the nitrogen atom to which they are attached, is piperidine or piperazine, unsubstituted or substituted by lower alkyl or lower hydroxyalkyl.

5. The compound of claim 1, in which $R_1$ is hydrogen, $R_2$ is methyl and $R_3$ is

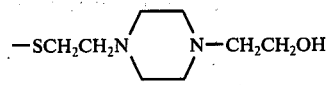

and chemotherapeutically acceptable acid addition salts thereof.

6. The compound of claim 1, in which $R_1$ is hydrogen, $R_2$ is methyl and $R_3$ is —SCH$_2$CH$_2$N(C$_2$H$_5$)$_2$ and chemotherapeutically acceptable acid addition salts thereof.

7. A chemotherapeutic composition useful in treating parasitic disorders and inhibiting mycoplasma growth comprising a chemotherapeutically effective amount of compound of claim 1, in association with a chemotherapeutically acceptable diluent or carrier.

8. A method of treating parasitic disorders comprising administering to a subject in need of such treatment an effective amount of a compound of claim 1.

9. A method of inhibiting mycoplasma growth, comprising administering to a subject in need of such treatment an effective amount of a compound of claim 1.

10. The compound of claim 1 which is 2-(1-Methyl-5-nitro-2-imidazolyl)-4-{2-[(2-hydroxyethyl)amino]ethoxy}quinazoline.

11. The compound of claim 1 in which $R_1$, $R_2$, and $R_3$ are H, CH$_3$, and

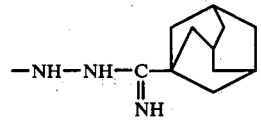

respectively.

12. The compound of claim 1 in which $R_1$, $R_2$ and $R_3$ are H, CH$_3$, and

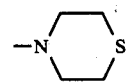

respectively.

13. The compound of claim 1 in which $R_1$, $R_2$ and $R_3$ are H, CH$_3$, and

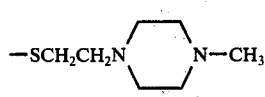

respectively.

14. The compound of claim 1 in which $R_1$, $R_2$ and $R_3$ are H, CH$_3$, and

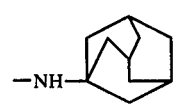

15. The compound of claim 1 in which $R_1$, $R_2$ and $R_3$ are H, $CH_3$, and

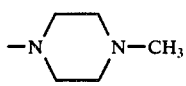

respectively.

16. The compound of claim 1 in which $R_1$, $R_2$ and $R_3$ are H, $CH_3$ and

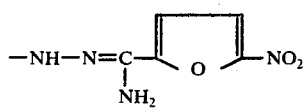

respectively.

17. The compound of claim 1 in which $R_1$, $R_2$ and $R_3$ are H, $CH_3$, and $OCH(CH_3)CH_2NHCH_2CH(CH_3)OH$ respectively.

18. The compound of claim 1 in which $R_1$, $R_2$ and $R_3$ are H, $CH_3$, and $-NHCH_2CH_2OH$ respectively.

19. The compound of claim 1 in which $R_1$, $R_2$ and $R_3$ are 7-Cl, $CH_3$, and $-OCH_2CH_2NHCH_2CH_2OH$ respectively.

20. The compound of claim 1 in which $R_1$, $R_2$ and $R_3$ are 6—$CH_3$, $CH_3$, and $-OCH_2CH_2NHCH_2CH_2OH$ respectively.

21. The compound of claim 1 in which $R_1$, $R_2$ and $R_3$ are 6—$CH_3$, $CH_3$, and

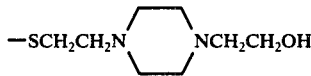

respectively.

22. The compound of claim 1 in which $R_1$, $R_2$ and $R_3$ are H, $CH_3$, and

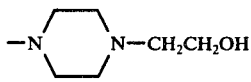

respectively.

23. The compound of claim 1 in which $R_1$, $R_2$ and $R_3$ are H, $CH_3$, and

respectively.

24. The compound of claim 1 in which $R_1$, $R_2$ and $R_3$ are H, $CH_3$, and $-N(CH_3)CH_2CH_2OH$ respectively.

25. The compound of claim 1 in which $R_1$, $R_2$ and $R_3$ are H, $CH_3$, and

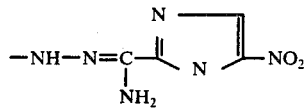

respectively.

26. The compound of claim 1 in which $R_1$, $R_2$ and $R_3$ are H, $CH_3$, and

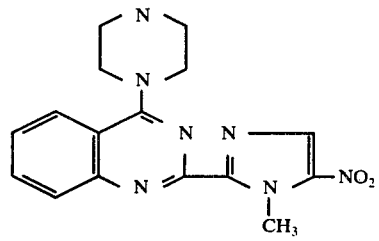

respectively.

27. The compound of claim 1 in which $R_1$, $R_2$ and $R_3$ are 6—Cl, $CH_3$, and

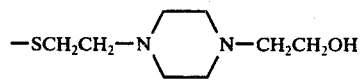

respectively.

28. The compound of claim 1 in which $R_1$, $R_2$ and $R_3$ are 6—Cl, $CH_3$, and $-OCH_2CH_2NHCH_2CH_2OH$ respectively.

29. The compound of claim 1 in which $R_1$, $R_2$ and $R_3$ are 7—Cl, $CH_3$, and

respectively.

30. The compound of claim 1 which is $R_1$, $R_2$ and $R_3$ are H, $CH_3$, and $-SCH_2CH_2N(C_2H_5)CH_2CH_2OH$ respectively.

31. The compound of claim 1 which is 2-(1-Methyl-5-nitro-2-imidazolyl)-4-[N-di-(2-hydroxyethyl)amino]-quinazoline.

* * * * *